United States Patent
Engell et al.

(10) Patent No.: US 10,660,966 B2
(45) Date of Patent: May 26, 2020

(54) METHOD FOR REMOVING ACETALDEHYDE

(71) Applicant: GE Healthcare Limited, Buckinghamshire (GB)

(72) Inventors: Torgrim Engell, Oslo (NO); Julian Grigg, Amersham (GB); Dimitrios Mantzilas, Oslo (NO); Dag M. Evje, Oslon (NO)

(73) Assignee: GE HEALTHCARE LIMITED, Buckinghamshire (GB)

( * ) Notice: Subject to any disclaimer, the term of this patent is extended or adjusted under 35 U.S.C. 154(b) by 86 days.

(21) Appl. No.: 15/532,938

(22) PCT Filed: Dec. 4, 2015

(86) PCT No.: PCT/EP2015/078682
§ 371 (c)(1),
(2) Date: Jun. 2, 2017

(87) PCT Pub. No.: WO2016/087653
PCT Pub. Date: Jun. 9, 2016

(65) Prior Publication Data
US 2017/0360943 A1 Dec. 21, 2017

Related U.S. Application Data

(60) Provisional application No. 62/087,371, filed on Dec. 4, 2014.

(51) Int. Cl.
| | | |
|---|---|---|
| *A61K 47/42* | (2017.01) | |
| *A61K 51/04* | (2006.01) | |
| *A61K 51/08* | (2006.01) | |
| *A61K 47/64* | (2017.01) | |
| *A61K 41/00* | (2020.01) | |
| *A61K 51/00* | (2006.01) | |

(52) U.S. Cl.
CPC .............. *A61K 47/42* (2013.01); *A61K 47/64* (2017.08); *A61K 51/0446* (2013.01); *A61K 51/0453* (2013.01); *A61K 51/082* (2013.01); *A61K 41/0038* (2013.01); *A61K 51/00* (2013.01)

(58) Field of Classification Search
None
See application file for complete search history.

(56) References Cited

U.S. PATENT DOCUMENTS

| | | | |
|---|---|---|---|
| 2005/0267222 A1 | 12/2005 | Iwata et al. | |
| 2015/0291699 A1* | 10/2015 | Bertozzi | C07D 311/92 530/391.1 |

FOREIGN PATENT DOCUMENTS

| | | |
|---|---|---|
| JP | 06503790 A | 4/1994 |
| JP | 2004073377 A | 3/2004 |
| JP | 2008500283 A | 1/2008 |
| JP | 2014500268 A | 1/2014 |
| RU | 2095085 C1 | 11/1997 |
| WO | 9210747 A1 | 6/1992 |
| WO | 2004037293 A1 | 5/2004 |
| WO | 2005107819 A2 | 11/2005 |
| WO | 2012076697 A1 | 6/2012 |
| WO | 2016087653 A1 | 6/2016 |

OTHER PUBLICATIONS

International Search Report and the Written Opinion of the International Searching Authority, or the Declaration from International Appl. No. PCT/EP2015/078682, dated Feb. 18, 2016.
Russia Office Action corresponding to Russian Application No. 2017116966/05, dated May 14, 2019.
Russia Search Report corresponding to Russian Application No. 2017116966/05, dated May 14, 2019.
Russia Decision to Grant a Patent for an Invention corresponding to Russian Application No. 2017116966/05, dated Feb. 14, 2020.
Japan Notice of Reasons for Rejection corresponding to Japanese Application No. 2017527839, dated Dec. 16, 2019.
"Succeeded in practical realization of apparatus for automated extraction of sugar chains from biological samples", JST (Japan Science and Technology Agency) Press Release, [URL: https://www.jst.go.jp/pr/announce/20111101/index.html] Nov. 1, 2011, pp. 2-10.

* cited by examiner

*Primary Examiner* — James W Rogers
(74) *Attorney, Agent, or Firm* — Arent Fox, LLP

(57) ABSTRACT

A method for removing or controlling or quantifying the presence of aldehydes, in particular acetaldehyde, is described. Such a method is useful in prolonging the shelf life of a pharmaceutical product.

7 Claims, 1 Drawing Sheet

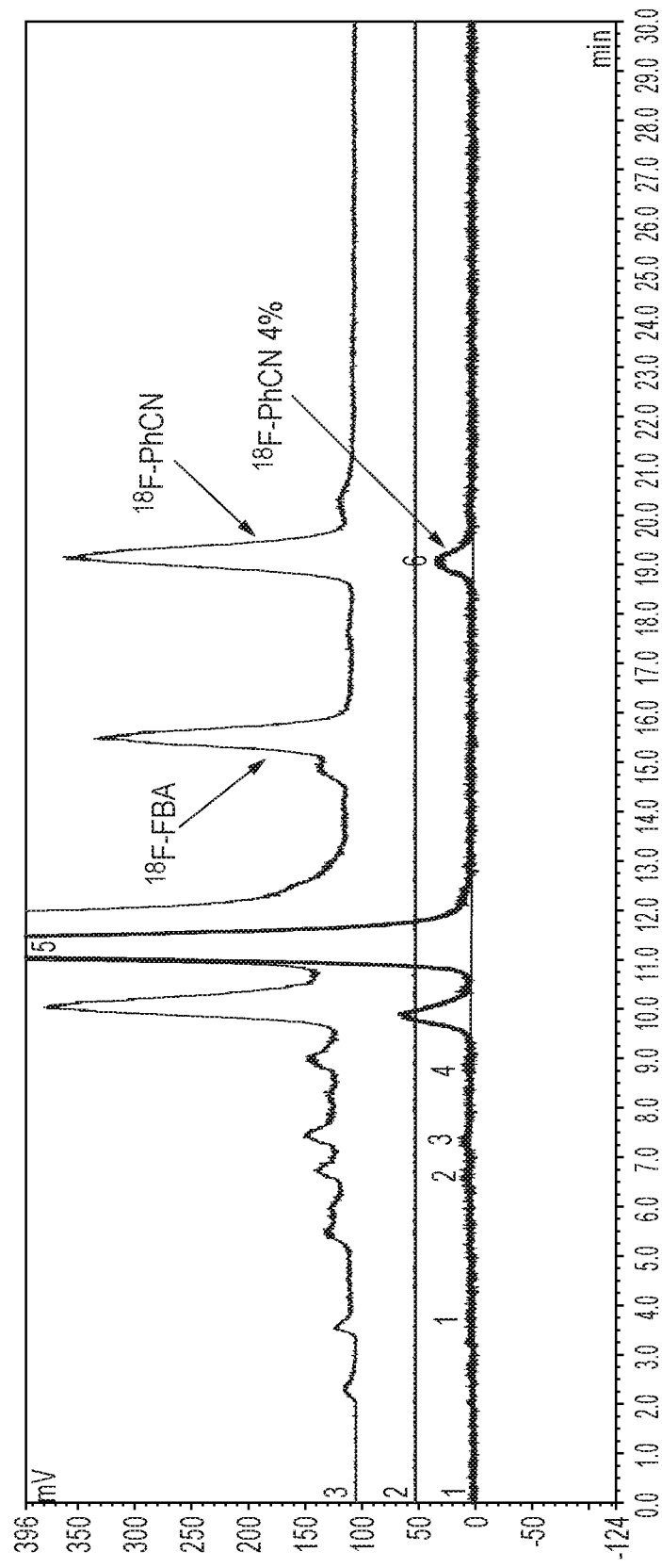

METHOD FOR REMOVING ACETALDEHYDE

FIELD OF THE INVENTION

The present invention relates to methods for removing or controlling the formation of aldehydes, and for their quantification. In particular, the present invention relates to a method for removing and/or controlling and/or quantifying the formation of acetaldehyde.

BACKGROUND OF THE INVENTION

Acetaldehyde is often found in the final formulation of a radioactive pharmaceutical. The rate of acetaldehyde formation increases with increased radioactivity. There are several sources for formation of acetaldehyde; ethanol is one of the most important sources. Acetaldehyde is most likely formed by oxidation of ethanol. This oxidation increases in a radioactive environment. In a worst case scenario formation of acetaldehyde might limit the maximum possible radiochemical concentration (RAC) and hence both the number of patient doses and product shelf-life. Further, acetaldehyde levels increase in time over the shelf-life of a radioactive pharmaceutical. As such, the level of acetaldehyde cannot be controlled by the manufacturing process of the radioactive pharmaceutical itself.

Thus there exists a need in the art for a method of quantifying and/or removing and/or controlling the formation of acetaldehyde in order to ensure that acetaldehyde levels remain within acceptable limits in order to prolong the shelf life of the radioactive pharmaceutical. The present invention answers such a need.

SUMMARY OF THE INVENTION

The present invention provides a method of quantifying and/or removing and/or controlling the level of acetaldehyde to be within acceptable limits (i.e. 120 µg/10 µl; Muller et al, Regulatory Toxicology and Pharmacology, 44, (2006), 198-211) in a final radioactive pharmaceutical formulation. In particular, the present invention provides a method of quantifying and/or removing and/or controlling the level of acetaldehyde during a radioactive pharmaceutical's shelf-life by introducing an aldehyde scavenger. The present method of the invention may also be used to measure and remove other by-products (e.g. other aldehydes, ketones) found in final radioactive pharmaceutical formulation.

The method of the invention can specifically by used for determination for quality control (QC) purposes of trace amounts of acetaldehyde in radioactive pharmaceutical formulations as an alternative to gas chromatography (GC). Measurement of residual acetaldehyde by GC is complicated by the presence of ethanol in pharmaceutical formulations due to its relatively large peak, and the method of the present invention overcomes this problem. It can also be used for determination of acetaldehyde in ethanol. Derivatives arriving from reaction between aminoxy and aldehyde or ketone can be designed to be a molecule which will increase both sensitivity and separation.

By quantifying and/or removing and/or controlling the formation of acetaldehyde by a method of the invention, the level of acetaldehyde in a pharmaceutical formulation, as defined herein, can remain within acceptable standard limits and thus an increased radiochemical concentration (RAC) may be achieved which in turn may maximize the number of patient doses from a single batch of a radioactive pharmaceutical formulation. The present invention permits simplification and improvement for quality control (QC)-methods for determination of trace amounts of aldehydes and ketones found in various pharmaceutical formulations.

These and other aspects of the invention will become apparent from the following detailed description of the preferred embodiments, taken in conjunction with the FIGURE.

BRIEF DESCRIPTION OF THE DRAWINGS

FIG. 1 shows the effect on RCP of the Fluciclatide ($^{18}$F) Injection, by quench with aldehyde scavenger AH111695.

DETAILED DESCRIPTION OF THE PREFERRED EMBODIMENTS

To more clearly and concisely describe and point out the subject matter of the claimed invention, definitions are provided hereinbelow for specific terms used throughout the present specification and claims. Any exemplification of specific terms herein should be considered as a non-limiting example.

The terms "comprising" or "comprises" have their conventional meaning throughout this application and imply that the agent or composition must have the essential features or components listed, but that others may be present in addition. The term 'comprising' includes as a preferred subset "consisting essentially of" which means that the composition has the components listed without other features or components being present.

The present invention provides a method for quantifying and/or removing and/or controlling acetaldehyde formation in a pharmaceutical formulation.

The present invention provides a method comprising the step of combining an aldehyde scavenger with a pharmaceutical formulation.

The present invention provides a method comprising the step of combining an aldehyde scavenger with a pharmaceutical formulation wherein the pharmaceutical formulation comprises a radioactive pharmaceutical and a solvent.

The present invention provides a composition comprising an aldehyde scavenger, a radioactive pharmaceutical and a solvent.

Aldehyde Scavenger

According to the invention, the aldehyde scavenger may be any molecule that has an amino-oxy terminus. The amino-oxy functional group is known to be extremely reactive allowing near full conversion of e.g. acetone in a concentration of 1 ppm at room temperature.

According to the invention, the aldehyde scavenger can quantify and/or control acetaldehyde levels and/or thereby permit removal of acetaldehyde from a pharmaceutical formulation until the levels are within acceptable industry standard limits. According to the invention, the aldehyde scavenger can equally be applied to other by-products (e.g. other aldehydes such as fluorobenzaldehyde (FBA), ketones) found in a pharmaceutical formulation.

In an embodiment of the invention, the aldehyde scavenger is the following compound (herein also referred to as "AH111695"; Mol. Wt. 1709.92):

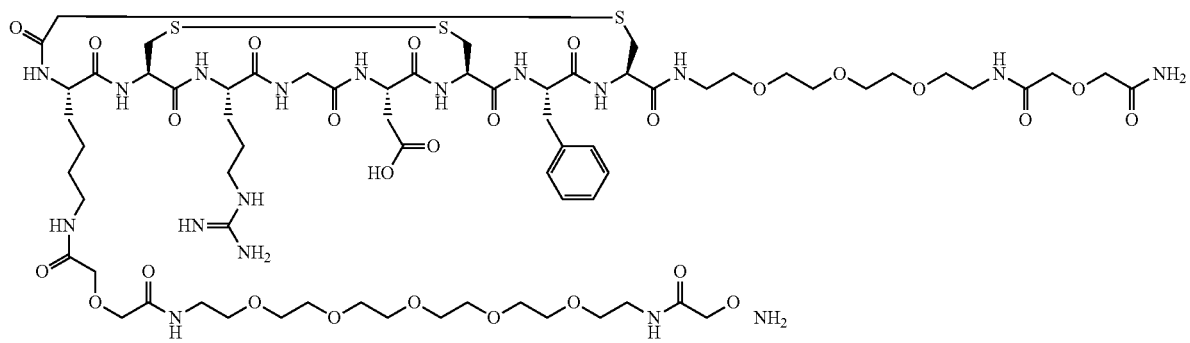

According to the invention, the acetaldehyde scavenger may be presented to the pharmaceutical formulation in a variety of manners. For example, the acetaldehyde scavenger may be presented as:

(i) a free aminoxy-containing excipient in the pharmaceutical formulation;

(ii) a solid-phase material containing the bound aminoxy-containing functionality through which the pharmaceutical formulation will be passed;

(iii) part of a cartridge/filtering unit as part of the dispensing fluid path used during the initial dispensing of the individual dose/QC/micro/retained sample vials;

(iv) part of a cartridge/filtering unit as part of the dispensing fluid path used to dispense just prior to clinical use;

(v) part of a cartridge/filtering unit that the pharmaceutical formulation is passed through when filling the syringe for patient dose administration soon after manufacture of the radiotracer; and/or (vi) a cartridge/filtering unit that the pharmaceutical formulation is passed through when filling the syringe for patient dose administration just prior to clinical use.

According to the invention, the aldehyde scavenger may also be added as an excipient in a pre-made formulation vial. Radioactive pharmaceuticals such as PET tracers are commonly transferred off an automated synthesis machine (e.g. FASTlab™) and into a pre-filled formulation vial to make the formulated production. According to this aspect of the invention, the aldehyde scavenger can be a part of this pre-filled formulation vial as an excipient.

According to the invention, the aldehyde scavenger may also be added as an excipient to a clinical vial. The pharmaceutical formulation, as described herein, is dispensed into different vials after formulation. If the aldehyde scavenger is solid particles, it cannot be dispensed since this dispensing includes sterile filtration. The solution to this is to present the scavenger as an excipient in the clinical vial (patient vial).

In the context of the quantification embodiment of the invention it should be noted that the imines formed in a reaction between an aminoxy and an aldehyde can be detected down to below 0.2 μg/ml equal to 0.1 nanomol e.g. for the PET tracer fluciclatide described herein by UV (the sensitivity by mass spectrometry would be even higher). 0.1 nanomol acetaldehyde corresponds to 0.0048 μg/ml acetaldehyde or 0.0048 ppm=4.8 ppb acetaldehyde. Below is illustrated a model reaction for quantification of acetaldehyde:

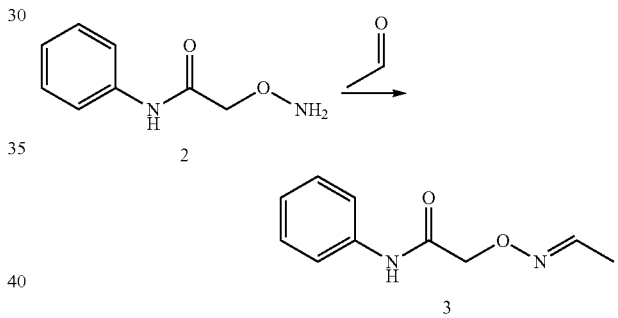

Molecular Weight: 192.21 The obtained molecule 3 can be analysed either by GC or HPLC. Separation of 3 from 2 is regarded as simple because of the great difference in polarity.

AH111930 illustrated below is the product between the aldehyde scavenger AH111695 described herein and acetaldehyde:

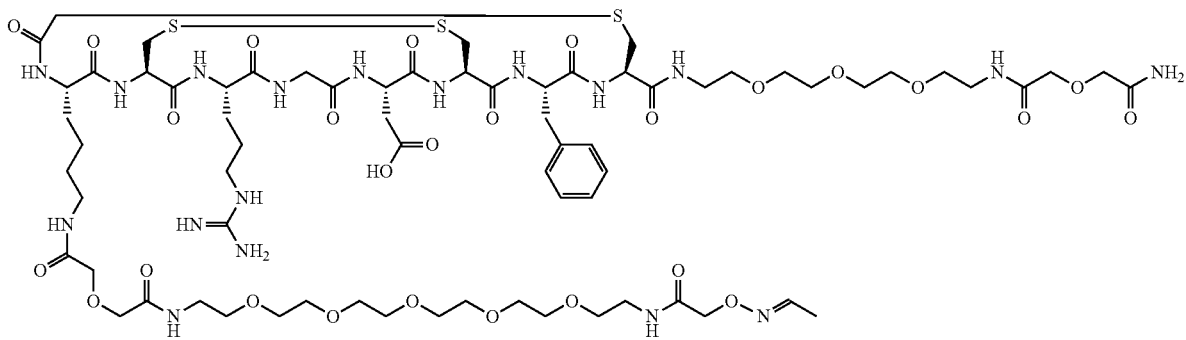

E-AH111930

AH111930 is formed during synthesis of fluciclatide described herein and is found in the crude reaction mixture in various amounts depending on the content of acetaldehyde e.g. in the ethanol used during process. AH111930 is typically reduced less to than 1-2 µg/ml over the final purification step. The amount of AH111930 in the final product is determined by the QC HPLC method during release of Fluciclatide ($^{18}$F) Injection. All unreacted AH111695 is removed during purification and hence acetaldehyde will remain unreacted if formed post-purification. The amount of acetaldehyde formed during storage of the pharmaceutical formulation can be determined by adding some AH111695 to a sample and heat for 10 min. The sample can then be analysed using the QC HPLC method and the content of AH111930 quantified and compared with release analysis. AH111930 might have a response at 216 nm lower than fluciclatide used as standard, but the response ratio between the two can be determined and AH111585 still be used as the standard.

Pharmaceutical Formulation

According to the invention a pharmaceutical formulation shall refer to any final radioactive pharmaceutical formulation. In one embodiment the pharmaceutical formulation is in a form suitable for mammalian administration, by which is meant a formulation which is sterile, pyrogen-free, lacks compounds which produce toxic or adverse effects, and is formulated at a biocompatible pH (approximately pH 4.0 to 10.5). Such formulations lack particulates which could risk causing emboli in vivo, and are formulated so that precipitation does not occur on contact with biological fluids (e.g. blood). Such formulations also contain only biologically compatible excipients, and are preferably isotonic. According to the invention a pharmaceutical formulation comprises a radioactive pharmaceutical and a solvent, each as described herein. A pharmaceutical formulation may be made by any means known in the art including, but not limited to, automated synthesis machines (e.g. FASTlab™).

Radioactive Pharmaceutical

According to the invention a radioactive pharmaceutical may comprise any radiolabelled compound suitable for in vitro or in vivo imaging. In one embodiment of the invention said radiolabelled compound is suitable for in vivo imaging. To be suitable for in vivo imaging a radioactive pharmaceutical is suitably provided in a form suitable for mammalian administration, and assists in providing clearer images in the region or organ of interest than could be obtained by imaging the mammalian subject alone. In a preferred embodiment, the radioactive pharmaceutical is a positron emission tomography (PET) tracer. In a preferred embodiment, the radioactive pharmaceutical is a $^{18}$F PET tracer. Non-limiting examples of suitable $^{18}$F PET tracers include, but are not limited to, [$^{18}$F]fluciclatide, [$^{18}$F]flutemetamol, and [$^{18}$F]GE180:

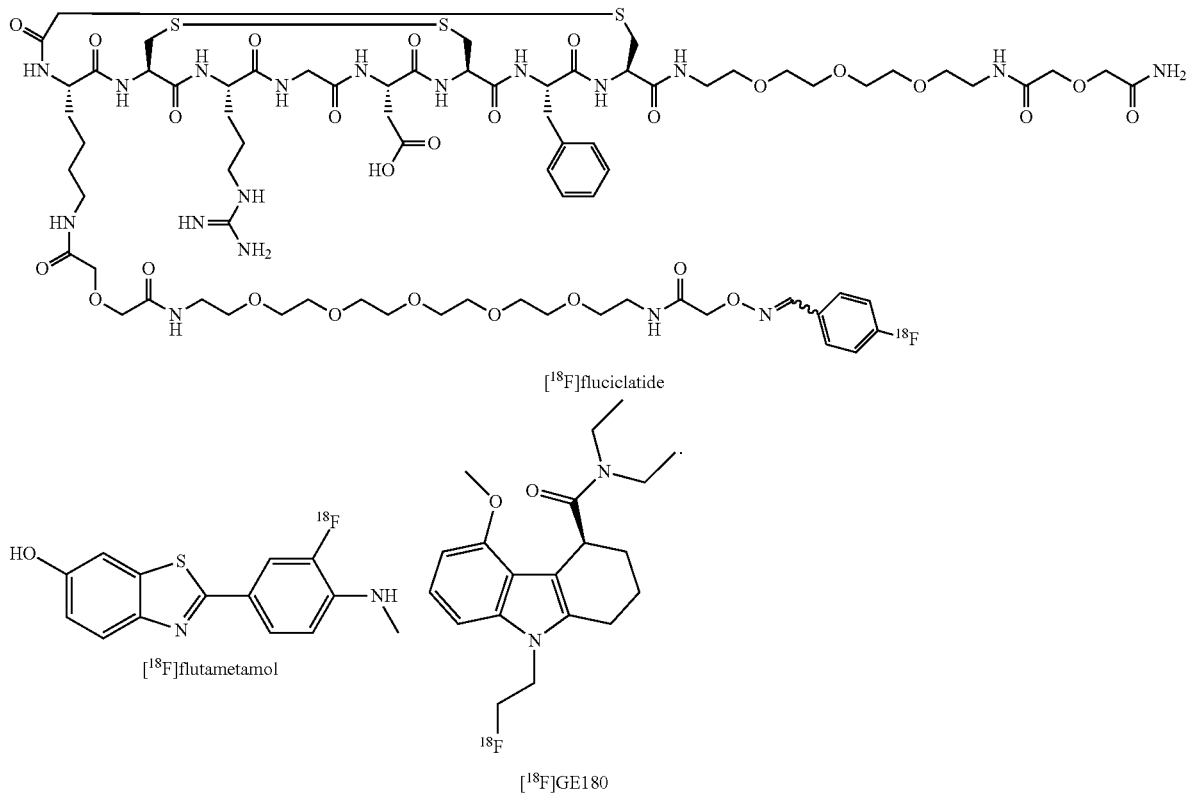

Methods suitable for production of [$^{18}$F]fluciclatide and formulations comprising [$^{18}$F]fluciclatide are described in WO 2004080492 A1, WO 2006030291 A2, WO 2012076697 A1 and US 20130209358 A1. In one embodiment of aspects of the present invention the $^{18}$F PET tracer is [$^{18}$F]fluciclatide.

Methods suitable for production of [$^{18}$F]flutametamol and formulations comprising [$^{18}$F]flutametamol are described in WO 2007020400 A1, WO 2009027452 A2 and WO 2011044406 A2. In one embodiment of aspects of the present invention the $^{18}$F PET tracer is [$^{18}$F]flutametamol.

Methods suitable for production of [$^{18}$F]GE180 and compositions comprising [$^{18}$F]GE180 are described in WO 2010109007 A2, WO 2011117421 A1 and WO 2012080349 A1. In one embodiment of aspects of the present invention the $^{18}$F PET tracer is [$^{18}$F]GE180.

Solvent

According to the invention, the solvent can comprise any organic solvent known in the art suitable for use in a pharmaceutical formulation. In a preferred embodiment, the solvent comprises an alcohol. In a preferred embodiment, the solvent is ethanol, isopropanol or a bioalcohol. In a preferred embodiment, the solvent is ethanol.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims. All patents and patent applications mentioned in the text are hereby incorporated by reference in their entireties, as if they were individually incorporated.

EXAMPLE 1

In an experiment to analyse the content of acetaldehyde in a Fluciclatide ($^{18}$F) Injection sample using HPLC, the acetaldeyde was derivatized to an UV absorbing fluciclatide analogue AH111930 using AH111695 (Scheme 1).

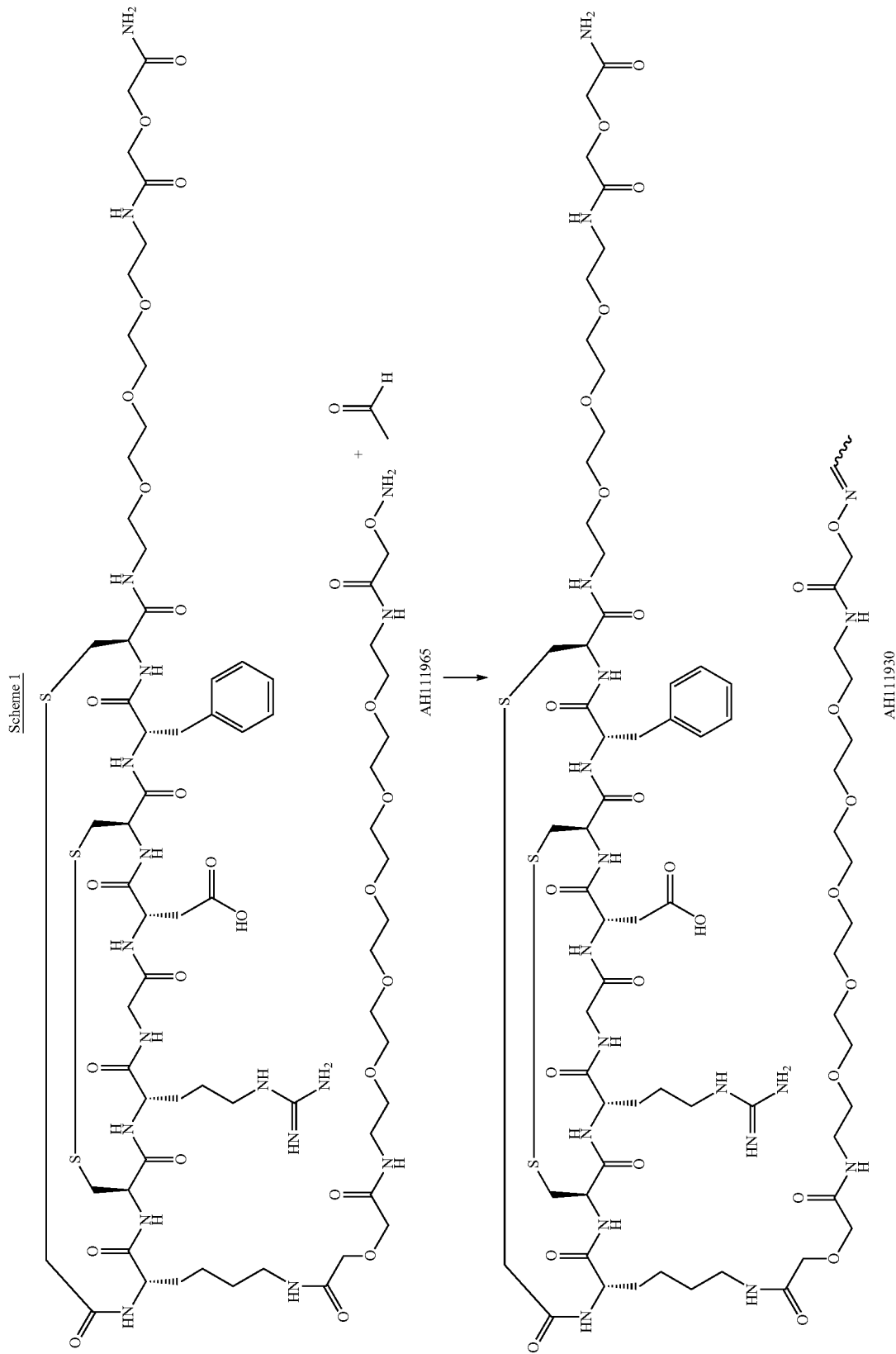

After 10 hours of decay, 0.5 ml sample of Fluciclatide ($^{18}$F) Injection was mixed with 0.5 ml of aqueous 1.6 mM AH111695/77.2 mM aniline HCl and heated to 60° C. for 30 min. The molar content of AH111930 was determined by HPLC and the amount of acetaldehyde quenched by AH111695 was found to be 7.6 μg/ml. In contrast, the amount of acetaldehyde in a control sample that was unquenched (i.e., no aldehyde scavenger AH111695 was added) was later determined by GC analysis to be 6.9 μg. The deviation between the HPLC and GC results is due to the higher sensitivity of the HPLC method over the GC method. The results indicate a complete quench of acetaldehyde was achieved by the addition of the aldehyde scavenger AH111695.

The quenched sample of Fluciclatide ($^{18}$F) Injection was also analysed for the content of the radio impurity 4-[$^{18}$F]fluorobenzaldehyde ([$^{18}$F]FBA) and the results were compared with an unquenched sample. The results showed that aldehyde scavenger AH111695 reacted with [$^{18}$F]FBA to form [$^{18}$F]fluciclatide removing the [$^{18}$F]FBA radio impurity from the product. This had a profound effect on the radiochemical purity (RCP). Analysis of 9 hours unquenched sample gave a RCP of 92.5% (initial RAC 1030 MBq/ml). After addition of aldehyde scavenger AH111695, the RCP increased to 94.5% (cis and trans isomers combined). Overlays of the radio chromatograms before and after quench are shown in FIG. 1. The two major radioimpurities are shown where [$^{18}$F]FBA was not detected in the quenched sample.

FIG. 1 clearly demonstrates the efficacy of the method in controlling aldehyde formation: (1) bottom trace is Fluciclatide ($^{18}$F) Injection quenched with aldehyde scavenger AH111695 after 9 hours; (2) middle trace is a blank; and (3) the top trace is Fluciclatide ($^{18}$F) Injection unquenched i.e., without addition of aldehyde scavenger AH111695, after 9 hours.

The invention claimed is:

1. A method for quantifying, removing or controlling acetaldehyde formation in a pharmaceutical formulation comprising the step of combining an aldehyde scavenger with a pharmaceutical formulation, wherein the pharmaceutical formulation comprises a radioactive pharmaceutical and a pharmaceutically acceptable solvent, wherein the aldehyde scavenger has the following structure:

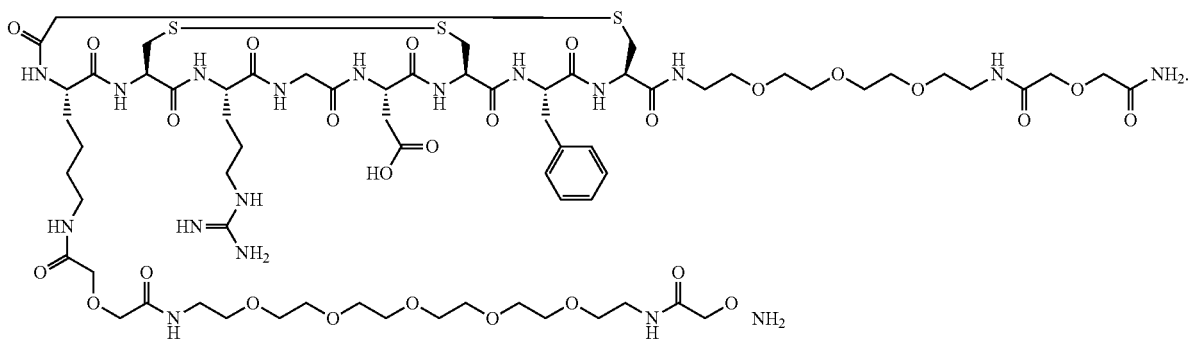

2. The method according to claim 1, wherein the radioactive pharmaceutical is a positron emission tomography (PET) tracer.

3. The method according to claim 1, wherein the radioactive pharmaceutical is a $^{18}$F PET tracer.

4. The method according to claim 1, wherein the radioactive pharmaceutical is elected from the group of compounds comprising:

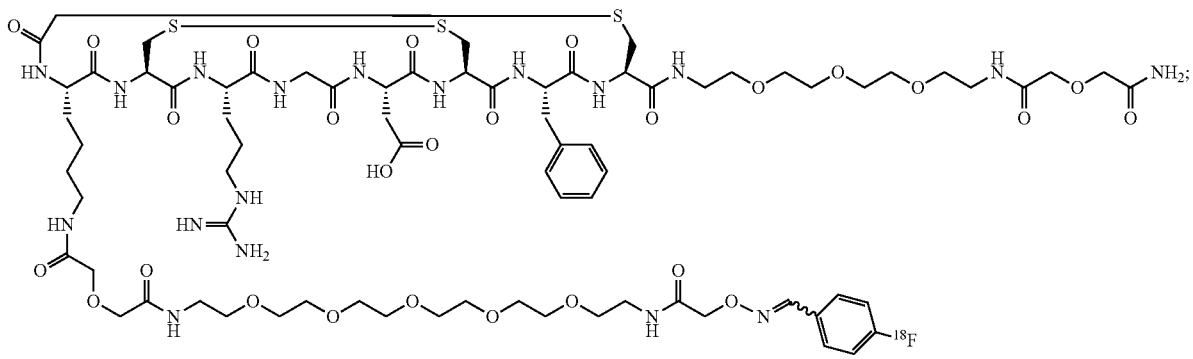

[$^{18}$F]fluciclatide

-continued
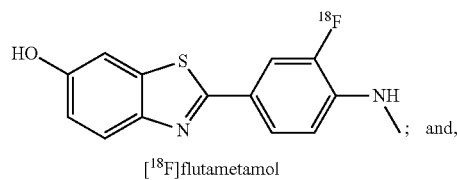
[¹⁸F]flutametamol
; and,
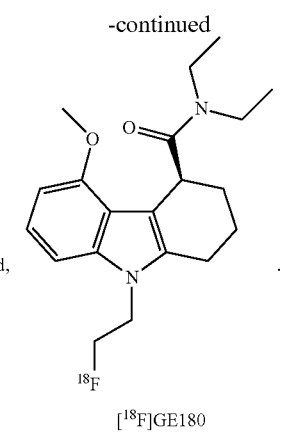
[¹⁸F]GE180
5. The method according to claim 1, wherein the solvent comprises an alcohol.
6. The method according to claim 5, wherein said alcohol is selected from ethanol, isopropanol or a bioalcohol.
7. The method according to claim 6, wherein said alcohol is ethanol.
* * * * *